United States Patent [19]
Walder

[11] Patent Number: 5,848,995
[45] Date of Patent: Dec. 15, 1998

[54] ANTI-INFECTIVE MEDICAL ARTICLE AND METHOD FOR ITS PREPARATION

[76] Inventor: Anthony J. Walder, 10081 Granite Crest La., Sandy, Utah 84092

[21] Appl. No.: 44,674

[22] Filed: Apr. 9, 1993

[51] Int. Cl.$^6$ .................................................. A61M 25/00
[52] U.S. Cl. ........................... 604/265; 424/618; 427/2.1
[58] Field of Search .................................... 604/265, 272, 604/273, 266, 163, 289, 264, 52, 53; 427/2; 424/617, 618, 619

[56] References Cited

U.S. PATENT DOCUMENTS

| | | | |
|---|---|---|---|
| 4,540,631 | 9/1985 | Boultinghouse . | |
| 4,592,920 | 6/1986 | Murtfeldt | 427/2 |
| 4,728,323 | 3/1988 | Matson . | |
| 4,849,223 | 7/1989 | Pratt et al. | 424/409 |
| 4,902,503 | 2/1990 | Umemura et al. . | |
| 4,973,320 | 11/1990 | Brenner et al. | 604/265 |
| 5,290,585 | 3/1994 | Elton | 427/2 |
| 5,320,908 | 6/1994 | Sodervall et al. | 428/461 |
| 5,331,027 | 7/1994 | Whitbourne | 524/37 |

FOREIGN PATENT DOCUMENTS

| | | | |
|---|---|---|---|
| 0777679 | 6/1957 | United Kingdom | 424/618 |
| 8401721 | 5/1984 | WIPO | 604/265 |

OTHER PUBLICATIONS

Gebelein, *Polymeric Materials and Artificial Organs,* 1984, pp. 13–29.

*Primary Examiner*—Corrine M. McDermott
*Attorney, Agent, or Firm*—Richard E. Brown

[57] ABSTRACT

An anti-infective medical article comprises a hydrophilic polymer having silver chloride bulk distributed therein. The hydrophilic polymer containing silver chloride may be a laminate over a base polymer. A method for making the article includes contacting the hydrophilic polymer with a solution of a soluble silver salt followed by a solution of a soluble chloride to give silver chloride bulk distributed throughout the polymer matrix. The polymer containing silver chloride may then be melt processed, such as by extruding or coextruding with the base polymer.

6 Claims, No Drawings

ANTI-INFECTIVE MEDICAL ARTICLE AND METHOD FOR ITS PREPARATION

BACKGROUND OF THE INVENTION

1. Field of the Invention

This invention relates to medical articles and their preparation, and more particularly relates to articles which inhibit or reduce bacterial growth during their use in a living body.

2. Background of the Invention

Plastic medical articles are often used internally in medical practice. A desirable feature of such articles is some means to control infection, which is often a complication when articles come into contact with a body tissue or fluid. Catheters, abdominal cavity tubing, drainage bags and various connectors are common sources of infection. In particular, a high percentage of patients who require long term urinary catheterization develop chronic urinary tract infections.

Many attempts to solve the problem of infection have been directed toward treatment of the article with an anti-infective agent. Antibiotics such as penicillin and antibacterials such as chlorhexidine and sulfadiazine have been used.

Silver has also long been used in clinical medicine because of its antiseptic properties. An extensive literature attests to the effectiveness of oligodynamic silver. Silver nitrate is well known for prophylaxis of ocular infections and treatment of burn wound sepsis.

In recent years, medical articles claimed to be infection-resistant due to silver salts associated therewith have been disclosed. Boultinghouse, in U.S. Pat. No. 4,540,631 discloses polymers coated with silver nitrate or having the silver nitrate blended therein. Matson, in U.S. Pat. No. 4,728,323 adhesively coats a wound dressing with a silver salt, as silver chloride. Murtfeldt, in U.S. Pat. No. 4,592,920 suspends silver oxide in a latex and dip coats the latex onto a catheter surface. Umemura et al. in U.S. Pat. No. 4,902,503 prepares anti-infective articles from a polymeric latex containing protein silver or a soluble silver salt. Brenner et al., in U.S. Pat. No. 4,973,320 discloses a bactericidal device and method therefor. The device has a very water soluble salt, such as silver, nitrate, in a polyurethane-silicone copolymer.

Although the above disclosures have addressed the problem of infection during use of medical articles, solutions which are fully satisfactory and economical to apply have not yet been achieved, particularly for articles, such as catheters. The present invention is directed toward providing a solution.

SUMMARY OF THE INVENTION

Silver chloride bulk distributed in a hydrophilic polyurethane (HPU) may be melt processed to give an antimicrobial medical article. In the present disclosure, the term hydrophilic means having a water absorption of 5% or more by weight. The term bulk distributed means substantially evenly distributed throughout the polymer. The HPU may be coextruded with a base polymer to give an article, preferably a tubing, having the silver chloride in only a thin laminated layer. The article of the invention may be made by a process in which a soluble silver salt is absorbed into the HPU matrix, and a soluble chloride absorbed thereafter.

The invention thus provides an antimicrobial medical article made by extrusion of an HPU matrix having silver chloride bulk distributed therein. Because of the low solubility of the silver chloride, the active agent is leached slowly when the article is contacted with a body fluid giving an antimicrobial effect of long duration.

DETAILED DESCRIPTION

When this invention is satisfied by embodiments in many different forms, there will herein be described in detail preferred embodiments of the invention with the understanding that the present disclosure is to be considered as exemplary of the principles of the invention and is not intended to limit the invention to the embodiments described. The scope of the invention will be measured by the appended claims and their equivalents.

The medical article having bulk distributed silver chloride of the invention may be used in a number of applications. For example, the article may be a film, useful as a wound dressing or surgical drape, a vascular graft, catheter introducer, obturator, or a tubing suitable for all catheter applications, such as a central venous access catheter, peripheral catheter or hemodialysis catheter. A particularly preferred article of the invention is a urinary catheter.

The article of the invention may be fabricated of a hydrophilic polymer. Suitable hydrophilic polymers are, for example, polyvinyl alcohol-polyvinyl acetate copolymers, polymethylmethacrylate-acrylic acid copolymers, 2-hydroxyethyl acrylate-polymethylmethacrylate copolymers and the like. The preferred hydrophilic polymer is a melt processable polyurethane. Suitable polyurethanes may be synthesized from three or more components including a polyisocyanate, a polyglycol soft segment and a chain extender.

Polyisocyanates useful in the present invention may have two or more isocyanate groups. Preferred polyisocyanates are aromatic or alicyclic diisocyanates, such as 4,4'-diphenylmethane diisocyanate, (MDI), toluene diisocyanate, isophorone di isocyanate, 4,4'-dicyclohexylmethane di isocyanate, hexamethylene diisocyanate and the like. Of these, aromatic diisocyanates are preferred, most preferably MDI.

The soft segment of the polyurethane may be a substantially hydrophilic polyglycol having a molecular weight of 500 to 16,000, preferably about 1000 to 8000. The polyglycol may be a polyester glycol or preferably a polyether glycol. The most preferred polyglycol is polyethylene oxide glycol (PEG), optionally mixed with another polyglycol, such as up to 50% of polytetramethylene ether glycol (PTMEG) such that the mixed polyglycol has a water absorption of at least 5%, preferably about 10–30% by weight.

The chain extender may be water and/or a low molecular weight branched or unbranched diol, diamine or aminoalcohol of up to 10 carbon atoms or mixtures thereof. Non-limiting examples of chain extenders are ethyleneglycol, 1,2-propanediol, 1,3-propanediol, 1,6-hexanediol, 1,4-bis-hydroxymethyl cyclohexane, ethanolamine, ethylenediamine, and preferably 1,4-butanediol (BDO).

The polyurethane may have a hard segment content of about 30–80%, preferably about 55–65% by weight wherein the term hard segment is used, in its conventional sense, to include the isocyanate and chain extender components.

In synthesizing the polyurethanes of the invention, the ratio of the ingredients which may be used is based on the reaction of one isocyanate group with one hydroxyl or amino group from the polyglycol or extender. Thus, the ratio of the total isocyanate groups in the diisocyanate to the total hydroxyl and amino groups present is conventionally referred to as the isocyante index (II) and may be from about 1.00 to 1.30 preferably from about 1.00 to 1.05, most preferably about 1.02. The quantities of the ingredients to be mixed may be calculated from the predetermined ratio of desired hard and soft segments and the known equivalent weights of the diisocyanate, polyglycol and extender. Synthesis of the polymer of the invention may be carried out by either a catalyst-free two step or prepolymer method of preferably by a catalyst-free one shot or bulk method. In the prepolymer method, the soft segment components are reacted with the diisocyanate to give a prepolymer having terminal isocyanate groups. The isocyanate-terminated prepolymer may then be reacted with the chain extender.

In one preferred bulk polymerization process of the invention, conventional polymerization equipment is charged with the extender and soft segment in proportions predetermined in accordance with the desired hard segment-soft segment ratio. With vigorous stirring, the diisocyanate may be added all at once. If the reaction does not start spontaneously, the mixture may be heated sufficiently to induce an exothermic reaction. The reaction mixture may be stirred vigorously until the exotherm is complete and the temperature begins to drop off, generally for about 1 to 5 minutes. The clear homogeneous melt, while still hot, may advantageously be removed from the reactor prior to curing. This procedure is described in detail in Example I.

In an alternative procedure, the soft segment and diisocyanate may be mixed with stirring, and, when the initial exotherm begins to subside, the extender may be added with continued stirring.

The reaction may be carried out for about 1 second to 10 minutes, preferably about 15 seconds to 5 minutes, most preferably for about 1 to 2 minutes. In general, the exotherm reaches about 100° C. before subsiding.

Any conventional method may be used to effect curing. Preferably, the melt is simply set aside for a suitable time and temperature, as, for example, from ambient to about 125° C. and for about 1 hour to 20 days to be cured with water present as atmospheric moisture.

Any conventional polymerization equipment or technique which provides vigorous stirring of the reactants and a clear melt at the conclusion of the exotherm may be used. Preferred equipment includes a multi-paddle shaft driven at high rotation rate by a motor. The cured polyurethane may preferably be chipped or pelletized for convenience in treating with silver salt. In accordance with the invention, it has been found that an insoluble silver salt, such as silver bromide or preferably silver chloride, can be bulk distributed in an HPU and the HPU melt processed to give an antimicrobial medical article. Bulk distribution of silver chloride may be accomplished by various methods. Thus the HPU and the silver chloride may be thoroughly mixed by tumbling the two components in powdered form prior to melt processing. In another process, the salt and HPU may be dissolved in a solvent such as dimethylacetamide or dimethylformamide, the solution cast into a film, and the solvent removed to leave a material suitable for melt processing.

In the preferred method for bulk distribution, the HPU, preferably in pellet form, is contacted with an aqueous solution of a soluble silver salt, such as the nitrate or acetate. Because of the hydrophilicity of the HPU, the soluble salt is absorbed into the polymer matrix. The pellets may then be rinsed and soaked in a solution of a soluble chloride, such as sodium or potassium chloride. The chloride ions pass into the HPU matrix, react with the soluble silver salt therein and precipitate in the matrix as silver chloride. The pellets may then be rinsed, dried and melt processed. Suitable melt processing techniques include molding, melt casting and preferably extrusion.

It has been found that the HPU having about 0.1 to 1.0, preferably about 0.3 to 0.8, most preferably about 0.5 weight percent of silver chloride may be melt processed into antimicrobial articles without loss of desirable physical properties, such as tensile, modulus and elongation. Further, the physical appearance of the articles is substantially unchanged from control articles made by melt processing control HPU with no silver chloride. Higher percentages of silver chloride up to 2.0 do not cause deterioration of the physical properties but may cause less satisfactory appearance due to visible scoring resulting from silver chloride particles. The articles exhibit excellent antimicrobial effect as determined by the conventional zone-of-inhibition test (described in detail in Example IV).

While the melt processed article described above gives fully satisfactory physical properties and antimicrobial performance, equally satisfactory results can be obtained by laminating the HPU containing silver chloride over a base polymer. In this preferred embodiment of the invention, the laminate may be kept thin as disclosed below, with no loss of antimicrobial effect, and a substantial saving in the amount of silver required may be achieved.

Any base polymer having suitable physical properties (tensile, modulus, elongation) and compatibility with the HPU for coextrusion may be used. Thus, suitable base polymers are substantially nonhydrophilic polyolefins, such as polypropylene and polyethylene, polyvinylchloride and preferably a polyurethane. The most preferred base polymer is a substantially non-hydrophilic polyurethane having a water absorption of about 0 to 3, preferably about 1 to 2 weight percent. This polyurethane may be made from the isocyanates and chain extenders described above for the HPU and a soft segment having from about 50 to 100, preferably 80–100% by weight PTMEG. Base polyurethanes may be made as described above and in Example I.

Coextrusion of the base polyurethane and the HPU may be carried out using conventional extrusion equipment, such as Killion or Entwisle extruders equipped with a die of appropriate orifice.

The invention contemplates extruded tubing having a gauge of 24 to 10 French. For the preferred laminated tubing, the laminate may be about 0.002 to 0.15mm preferably about 0.02 to 0.06mm thick.

Prior to melt processing, conventional additives such as stabilizers, radiopaque materials such as barium sulfate, and the like may be included. The additive may be incorporated into either or both of the base polyurethane or the HPU. The radiopaque agent may be included as coextruded stripes, as is well-known in the catheter art, or may be bulk distributed. The amounts of these materials will vary depending upon the application of the polyurethane, but they are typically present in amounts ranging from about 20 to 40% of the polymer blend.

The silver chloride in the catheter of the invention is leached slowly because of the very low solubility of the salt. This slow leach rate, while sufficient to produce a suitable anti-infective catheter, has the advantage of providing anti-infective activity of long duration. In contrast, surface coatings or bulk distributions of soluble salts give articles in which the anti-infectiveness is of short duration.

The following examples are provided to further illustrate the invention but are not to be considered as limitative of the invention.

EXAMPLE I
General Procedure For Polyurethane Synthesis

The calculated quantities of polyglycol and diol extender required to prepare a polyurethane having the desired hard segment content were combined in a resin bottle at 60° C., and vacuum stripped for 16 hours and 50°–55° C. at 1–2 mm Hg. The mixture was cooled to ambient temperature and the calculated amount of filtered diisocyanate, based on total hydroxyl content, was added all at once with vigorous stirring. The exotherm reached about 80° C., whereupon the mixture was poured into a teflon-lined tray and post-cured at 125° C. for about 60 minutes.

In an alternative procedure, the polyglycol and diisocyanate may be mixed with stirring, and, when the initial exotherm begins to subside, the extender may be added with continued stirring.

EXAMPLE II
Bulk Distribution of Silver Salt in HPU Tubing

HPU pellets from MDI, BDO and PEG 1450 and PEG 8000 were soaked in a 0.1N aqueous solution of silver nitrate for 1 minute, washed, air dried, soaked in normal saline for various times, washed and air dried. The pellets were tested by the procedure of Example IV and gave the following results:

| Soak Time | Zone of Inhibition (mm) | |
|---|---|---|
| (hr) | PEG 8000 | PEG 1450 |
| 2 | 7.7 | 5.3 |
| 4 | 8.0 | 4.0 |
| 8 | 7.3 | 4.3 |
| 24 | 8.0 | 3.3 |

Control HPU pellets devoid of silver salt give no zone of inhibition.

It is seen that greater zones of inhibition are formed by using the more hydrophilic PEG-8000 as the HPU soft segment.

EXAMPLE III
Coextruded Tubing with Silver Salt in Laminate

Various concentrations of aqueous silver nitrate were prepared. Pellets of a 40% hard segment HPU made from MDI, BDO and a 50:50 mixture of PEG-8000 and PEG-1450 were soaked in the silver nitrate solutions for 1 hour. The pellets were washed and dried at 50° C. for 6 hr. in a forced air oven, then soaked in normal saline for 6 hours and dried for 48 hr in a vacuum oven. The pellets were coextruded with a base polyurethane made from MDI, BDO and PTMEG to give tubings having different thicknesses of HPU laminate containing different percentages of chloride in the laminate. The tubings were tested for in vitro antimicrobial effectiveness by the procedure of Example IV. The following results were obtained:

| Polyurethane Tubing | Thickness of laminate (mm) | Silver Chloride % | Zone (mm) | Surface Appearance |
|---|---|---|---|---|
| control | 12.7 | 0 | 0 | very good[a] |
| 1 | 6.3 | 0.5 | 7.7 | good[b] |
| 2 | 12.7 | 0.5 | 7.2 | good |
| 3 | 6.3 | 1.0 | 7.2 | good |
| 4 | 12.7 | 1.0 | 7.2 | poor[c] |
| 5 | 12.7 | 2.0 | 7.2 | very poor[d] |

[a] - smooth, uniform glassy surface
[b] - as in (a) with faint extrusion lines*
[c] - uniform surface with noticeable extrusion lines
[d] - non-uniform surface with extrusion lines
* - scorings in tubing due to silver chloride particles

EXAMPLE IV
Test for Anti Infective Activity (In Vitro)

In vitro antimicrobial activity of the tubing of the invention was measured by a standard zone of inhibition test. A broth of the test organism, such as *S. aureus*, was started from standard disks (BACTROL™) in typticase soy broth (TSB) and allowed to grow overnight. A 0.2 ml aliquot of the overnight broth was transferred to a fresh solution of TSB and allowed to grow for 2 to 5 hours until the turbidity of the solution was equivalent to a 1% barium sulfate standard solution. A 0.2 ml aliquot of this broth was transferred to a Mueller-Hinton (M-H) agar plate and spread evenly on the surface. The polyurethane tubings of the invention were cut into lengths of 1.5 cm and embedded into the surface of the agar. The plates were then cultured 16 hours (overnight). Plates were evaluated for the inhibition of bacterial growth visually by the unaided eye. Zones were measured in millimeters across the axis of the tubing, the measurement including the diameter of the tubing.

Comparative Example V

The 40% hard segment HPU pellets of Example III were powdered and tumbled with 0.5% by weight silver oxide. Attempted extrusion of this material resulted in extensive decomposition and a black extrudate of uneven surface.

What is claimed is:

1. An anti-infective medical article comprising a hydrophilic polymer having an insoluble silver salt bulk distributed therein, said polymer having a water absorption of 5% or more by weight.

2. An anti-infective medical article comprising a first polymer and a layer of a second polymer laminated thereon, said second polymer being hydrophilic and having an insoluble silver salt bulk distributed therein, said second polymer having a water absorption of 5% or more by weight.

3. The article of claim 2 wherein said first polymer is selected from the group consisting of polyurethane, polyolefin and polyvinyl chloride.

4. The article of claim 2 wherein said second polymer is selected from the group consisting of polyurethane, polyvinyl alcohol-polyvinyl acetate copolymer, polymethylmethacrylate-acrylic acid copolymer and 2-hydroxyethyl acrylate-polymethylmethacrylate copolymer.

5. The article of claim 2 which is a tubing.

6. An anti-infective medical tubing comprising a first polyurethane and a layer of a second polyurethane laminated thereon, said second polyurethane being hydrophilic, having a water absorption of 5% or more by weight and having silver chloride bulk distributed therein.

* * * * *